United States Patent
Czernik et al.

(12)

(10) Patent No.: US 7,097,992 B2
(45) Date of Patent: Aug. 29, 2006

(54) USES OF HUMAN UDP-GLUCURONOSYLTRANSFERASE 2B7 TO DETECT AND TREAT CANCER

(76) Inventors: Piotr J. Czernik, 8710 Boulder La., Little Rock, AR (US) 72227; Anna Radominska-Pandya, #5 Bugle Ct., Little Rock, AR (US) 72207

( * ) Notice: Subject to any disclaimer, the term of this patent is extended or adjusted under 35 U.S.C. 154(b) by 488 days.

(21) Appl. No.: 10/132,499

(22) Filed: Apr. 25, 2002

(65) Prior Publication Data

US 2002/0198167 A1    Dec. 26, 2002

Related U.S. Application Data

(60) Provisional application No. 60/286,441, filed on Apr. 25, 2001, provisional application No. 60/292,376, filed on May 21, 2001.

(51) Int. Cl.
*G01N 33/53* (2006.01)
(52) U.S. Cl. .......................................... 435/7.23; 436/64
(58) Field of Classification Search ................. 435/7.3, 435/501
See application file for complete search history.

(56) References Cited

OTHER PUBLICATIONS

Radominska-Pandya et al., Arch Biochem Biophys. Mar. 1, 2002;399(1):37-48.*

* cited by examiner

*Primary Examiner*—Misook Yu
(74) *Attorney, Agent, or Firm*—Benjamin Aaron Adler

(57) ABSTRACT

Human UDP-glucuronosyltransferase 2B7 (UGT2B7) protein expression is limited to ovarian surface epithelium cells and that this protein is not present in tumors arising from this cell layer. UDP-glucuronosyltransferase 2B7 protein accumulates in cells when the cells enter stationary phase and growth inhibition. UGT2B7 protein is not expressed in exponentially growing ovarian tumor cells. Overexpression of UGT2B7 protein in human ovarian tumor cells results in cell growth arrest, significant reduction of lipid content and changes in cell morphology. Thus, active UGT2B7 protein expression in tumor cells can be used to decrease cell proliferation and to treat various cancers, whereas UGT2B7 mRNA expression, protein expression and/or enzymatic activity can be used as a tumor specific marker in diagnostic procedures.

2 Claims, 11 Drawing Sheets

USES OF HUMAN UDP-GLUCURONOSYLTRANSFERASE 2B7 TO DETECT AND TREAT CANCER

CROSS-REFERENCE TO RELATED APPLICATION

This is a non-provisional patent application claims benefit of provisional patent application U.S. Ser. No. 60/286,441, filed Apr. 25, 2001, U.S. Ser. No. 60/292,376 filed May 21, 2001 now abandoned.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the field of tumor biology. More specifically, the present invention relates to the use of human UDP-glucuronosyltransferase 2B7 to detect and treat cancer.

2. Description of the Related Art

UDP-glucuronosyltransferases (UGTs) comprise a family of enzymes involved in the detoxification of a variety of mostly hydrophobic endogenous and exogenous compounds. UGT isoenzymes are classified on the basis of sequence homology into two families: UGT1A and UGT2B. UGT2B enzymes catalyze the glucuronidation of bile acids, steroids, fatty acids retinoids, whereas UGT1A enzymes carry out the glucuronidation of bilirubin, phenols, various drugs and certain steroids (Radominska-Pandya et al., 1999; Jude et al., 2001). Recent studies suggested that UDP-glucuronosyltransferase proteins, in addition to their function as detoxification enzymes, are actively involved in biotransformations leading to the formation of toxic mutagens and carcinogens (Bock, 1991; Bock et al., 1999).

Environmental and other exogenous carcinogens have been implicated as a driving force for initiation of hyperproliferation and neoplastic transformation. UDP-glucuronosyltransferases play an important role in cellular detoxification and have been postulated to exert genoprotective properties.

Recent studies provided evidence for differential regulation of the UGT1A locus in human malignant and benign hepatic tumors (Strassburg et al., 1997). Functional reduction of UGT1A protein and glucuronidation activity was implicated in hepatic carcinogenesis, possibly by means of reducing cellular DNA protection. Another study examined the role of constitutional genetic variation at the UGT1A1 locus in breast cancer susceptibility. These studies suggested a link between UGT1A1 alleles, estrogen metabolism and breast cancer risk (Guillemette et al., 2000). Other evidence suggested that bilirubin plays a significant role as an antioxidant and the UGT1A1 gene plays a potential role in modulating oxidative damage and cancer (Grant & Bell, 2000).

It has been demonstrated that UDP-glucuronosyltransferase 2B7 protein was predominantly expressed in normal mammary epthelium, and that its expression was dramatically reduced in invasive breast cancers. It was postulated that UDP-glucuronosyltransferase 2B7 plays an important protective role in normal breast tissue by elimination of 4-hydroxy catecholestrogens (Gest1 et al., 2002). However, the expression and function of UDP-glucuronosyltransferase 2B7 in ovarian cancer cells have not been determined.

Human cancer tissues have the capacity to synthesize their own supply of fatty acid independent of the signals that down-regulate fatty acid synthesis in normal cells (Kuhajda, 2000). Ovarian cancer cells produce high amounts of lipid compounds including lysophospholipids, the activities of which have been linked to cancer development and metastasis (Xu et al., 2001). High level of lipid accumulation observed in ovarian cancer cells and the ability of UDP-glucuronosyltransferase 2B7 to interfere with lipid synthesis through glucuronidation of free fatty acids suggest UDP-glucuronosyltransferase 2B7 may have a role in regulating ovarian tumor cell growth.

However, the prior art is deficient in methods of using human UDP-glucuronosyltransferase 2B7 to detect and treat cancer. The present invention fulfills this long-standing need and desire in the art.

SUMMARY OF THE INVENTION

Human UDP-glucuronosyltransferase 2B7 (UGT2B7) protein expression is limited to ovarian surface epithelium cells and this protein is not present in tumors arising from this cell layer. UDP-glucuronosyltransferase 2B7 protein accumulates in cells when the cells enter stationary phase and growth inhibition. UDP-glucuronosyltransferase 2B7 is not expressed in exponentially growing ovarian tumor cells. Overexpression of UDP-glucuronosyltransferase 2B7 protein in human ovarian tumor cells results in cell growth arrest, significant reduction of lipid content and changes in cell morphology. Thus, expression of active UDP-glucuronosyltransferase 2B7 protein in tumor cells can be used to decrease cell proliferation and may be used to treat various cancers in combination with other treatments. Moreover, UDP-glucuronosyltransferase 2B7 mRNA expression, protein expression and/or enzymatic activity can be used as a tumor specific marker in diagnostic procedures.

In one aspect of the present invention, there is provided a method of inhibiting ovarian tumor cell growth by transfecting or infecting the cells with a vector encoding human UDP-glucuronosyltransferase 2B7 (UGT2B7).

In another aspect of the present invention, there are provided methods of detecting malignant ovarian hyperplasia in a biological sample by the detection of UDP-glucuronosyltransferase 2B7 mRNA or protein.

In yet another aspect of the present invention, there is provided a method of screening for compound that increases the enzymatic activity of UDP-glucuronosyltransferase 2B7.

In yet another aspect of the present invention, there is provided a method of increasing the expression of the endogenous UDP-glucuronosyltransferase 2B7 in organs or tissues (pre-malignant lesions, growing tumors, metastatic sites, etc.)

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1 shows the localization of UGT2B7 in normal and tumor tissues.

FIG. 2 shows the expression of UGT2B7 in JM cells.

FIG. 5 shows inhibition of cell proliferation of UGT2B7-transfected ovarian cancer cells.

FIG. 6 shows reduction of intracellular lipids in cells expressing UGT2B7.

DETAILED DESCRIPTION OF THE INVENTION

Figure 1A:
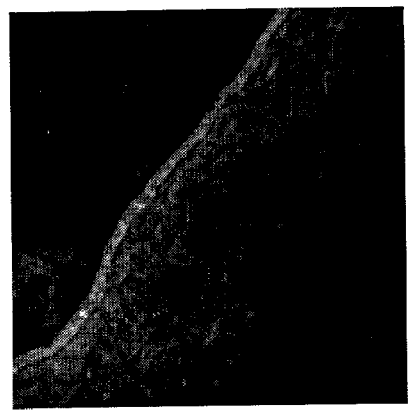
FIG. 1A shows normal tissue section containing ovarian surface epithelium (OSE) and cortex (C) (100× magnification).

The UDP-glucuronosyltransferase 2B7 (UGT2B7) protein is a major UDP-glucuronosyltransferase involved in glucuronidation of fatty acids and a variety of other endogenous compounds, including steroid hormones, bile acids, retinoids, drugs and xenobiotics. Immunofluorescent detection of UDP-glucuronosyltransferase 2B7 protein in normal ovarian tissue showed that this protein is predominantly expressed in ovarian surface epithelium. In contrast, in three independent ovarian tumor cell lines isolated from serous papillary adenocarcinomas which originates from ovarian surface epithelium, the UDP-glucuronosyltransferase 2B7 transcript was not detected using Northern blot analysis. Close examination of UDP-glucuronosyltransferase 2B7 protein expression in the ovarian tumor cell line by Western blot confirmed a lack of expression in the first 90 hours of growth; however, low level of UDP-glucuronosyltransferase 2B7 protein expression and very low UDP-glucuronosyltransferase 2B7 enzymatic activity, were detected in cells entering stationary phase. Stable expression of UDP-glucuronosyltransferase 2B7 cDNA in the ovarian tumor cells resulted in a 3-fold reduction of lipid content, cell growth arrest, and changes in colony formation. Inactivation of UDP-glucuronosyltransferase 2B7 mRNA by antisense oligonucleotides resulted in temporal acceleration of cell proliferation. Hence, downregulation of UDP-glucuronosyltransferase 2B7 in ovarian cells and concomitant accumulation of bioactive lipids can result in destabilization of fatty acid homeostasis and uncontrollable cell proliferation.

The present invention demonstrates that active UDP-glucuronosyltransferase 2B7 protein expression in tumor cells can be used to decrease cell proliferation and to treat various cancers, whereas UDP-glucuronosyltransferase 2B7 mRNA expression, protein expression and/or enzymatic activity can be used as a tumor specific marker in diagnostic procedures.

In accordance with the present invention there may be employed conventional molecular biology, microbiology, and recombinant DNA techniques within the skill of the art. Such techniques are explained fully in the literature. See e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

In the present invention, there is provided a method of inhibiting ovarian tumor cell growth by transfecting or infecting said cells with vector encoding human UDP-glucuronosyltransferase 2B7 (UGT2B7), wherein expression of UDP-glucuronosyltransferase 2B7 in the cells results in growth arrest of the tumor cells.

A "vector" may be defined as a replicable nucleic acid construct, e.g., a plasmid or viral nucleic acid. Vectors may be used to amplify and/or express nucleic acid encoding the UGT2B7 protein. An "expression vector" is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the present invention include, but are not limited to, plasmid vectors and viral vectors. Preferred viral vectors of the invention are those derived from retroviruses, adenovirus, adeno-associated virus, SV40 virus, or herpes viruses.

In another aspect of the present invention, there is provided a method of detecting malignant ovarian hyperplasia in a biological sample by isolating and detecting UDP-glucuronosyltransferase 2B7 mRNA in the sample. A decrease in UDP-glucuronosyltransferase 2B7 mRNA expression in the sample compared to that expressed in normal tissues is indicative of the presence of malignant ovarian hyperplasia in the sample. The UDP-glucuronosyltransferase 2B7 mRNA can be detected by PCR amplification, and the biological sample can be blood, interstitial fluid, ascites fluid, tumor tissue biopsy or circulating tumor cells. A standard Northern blot assay can also be used to ascertain the relative amounts of UDP-glucuronosyltransferase 2B7 mRNA in a cell or tissue obtained from a patient suspected of having cancer in accordance with conventional Northern hybridization techniques known to those persons of ordinary skill in the art.

The present invention is also directed to a method of detecting malignant ovarian hyperplasia in a biological sample by isolating and detecting UDP-glucuronosyltransferase 2B7 protein expression in said sample. A decrease of UDP-glucuronosyltransferase 2B7 protein expression in the sample compared to UDP-glucuronosyltransferase 2B7 protein expressed in normal tissues is indicative of the presence of malignant ovarian hyperplasia. The UDP-glucuronosyltransferase 2B7 protein can be detected by Western blot, and the biological sample can be blood, interstitial fluid, ascites fluid, tumor tissue biopsy or circulating tumor cells.

The present invention is further directed to a method of increasing expression of the endogenous UDP-glucuronosyltransferase 2B7 gene by stimulation of the UGT2B7 regulatory elements or pathways. This includes, but is not limited to, stimulation of the UGT2B7 promoter, enhancers, etc., and manipulation with transduction pathways involved in this regulation by using agonists or inhibitors for signal transduction receptors, protein kinases, etc.

In yet another aspect of the present invention, there is provided a method of screening for compound that increases the enzymatic activity of UDP-glucuronosyltransferase 2B7. A sample comprising UDP-glucuronosyltransferase 2B7 protein is treated with the test compound. An increase in UDP-glucuronosyltransferase 2B7 enzymatic activity in the presence of said compound relative to UDP-glucuronosyltransferase 2B7 enzymatic activity in the absence of said compound is indicative of a compound that increases UDP-glucuronosyltransferase 2B7 enzymatic activity.

The following examples are given for the purpose of illustrating various embodiments of the invention and are not meant to limit the present invention in any fashion.

EXAMPLE 1

Localization of UDP-Glucuronosyltransferase 2B7 Protein in Normal and Ovarian Tumor Tissue Almost all malignant ovarian tumors originate from a single ovarian surface epithelium cell. It was crucial for the present studies to determine the expression status of UDP-glucuronosyltransferase 2B7 protein in normal ovarian tissue and compare with its expression in ovarian tumor tissues. Immunofluorescent detection of UDP-glucuronosyltransferase 2B7 protein was carried out using TARP2 tissue microarrays obtained from National Cancer Institute, NIH. Microarrays containing several individual sections of normal tissue and 47 individual sections of ovarian tumors were stained with primary anti-UDP-glucuronosyltransferase 2B7 antibody (Gentest Corp.) and FITC-conjugated secondary antibody.

Figure 1B:
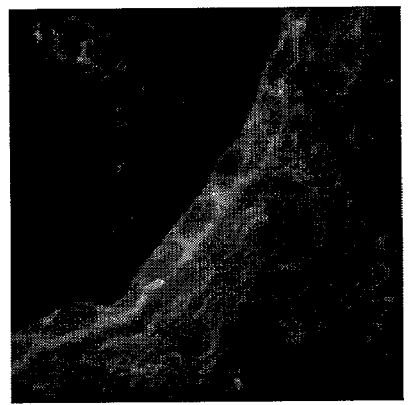
FIG. 1B shows normal ovarian surface epithelium at 600× magnification.
Figure 1C:
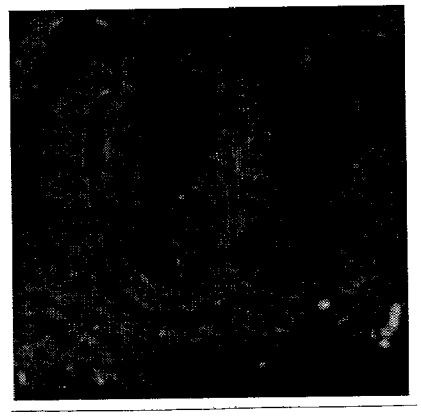
FIG. 1C shows ovarian papillary adenocarcimoma tissue section containing epithelial cells (E).

Two representative tissue specimens are shown in FIG. 1. Presented images (FIG. 1A, FIG. 1B) clearly show that UDP-glucuronosyltransferase 2B7 protein is predominantly expressed in ovarian surface epithelium cell, moderate amount of the protein is present in cortex and the protein is not detectable in ovarian stroma. UDP-glucuronosyltransferase 2B7 protein is not present in papillary adenocarcinoma tissue section (FIG. 1C) including cells of epithelial morphology. This experiment strongly indicates that expression of UDP-glucuronosyltransferase 2B7 may be limited to ovarian surface epithelium cells and that this protein is not present in tumors arising from this cell layer.

EXAMPLE 2

Characterization of UDP-Glucuronosyltransferase 2B7 Gene Expression in Ovarian Cancer Cells UDP-glucuronosyltransferase 2B7 gene expression was examined in three independent ovarian tumor cell lines, named JM, JW and BallardK, isolated from serous papillary adenocarcinomas that originate from ovarian surface epithelium. It was previously determined that microsomal fraction isolated from the JM cells lacked measurable UDP-glucuronosyltransferase 2B7 activity for androsterone, retinoic acid and linoleic acid, which are standard substrates for this isoform (data not shown).

To determine whether UDP-glucuronosyltransferase 2B7 was present in ovarian tumor cells, Western blot analysis for UDP-glucuronosyltransferase 2B7 protein expression was carried out during 192 hours of cell culture. One hundred mm plates were seeded with 100,000 cells per plate and the cells were harvested in 24 hour intervals. Total number of cells was determined for each interval, cell density was calculated and cell lysates were prepared from each time point for the analysis of UDP-glucuronosyltransferase 2B7 expression. During the experiment cells reached confluence between 120 and 144 hour of growth as monitored by microscopic observations.

Figure 2A:
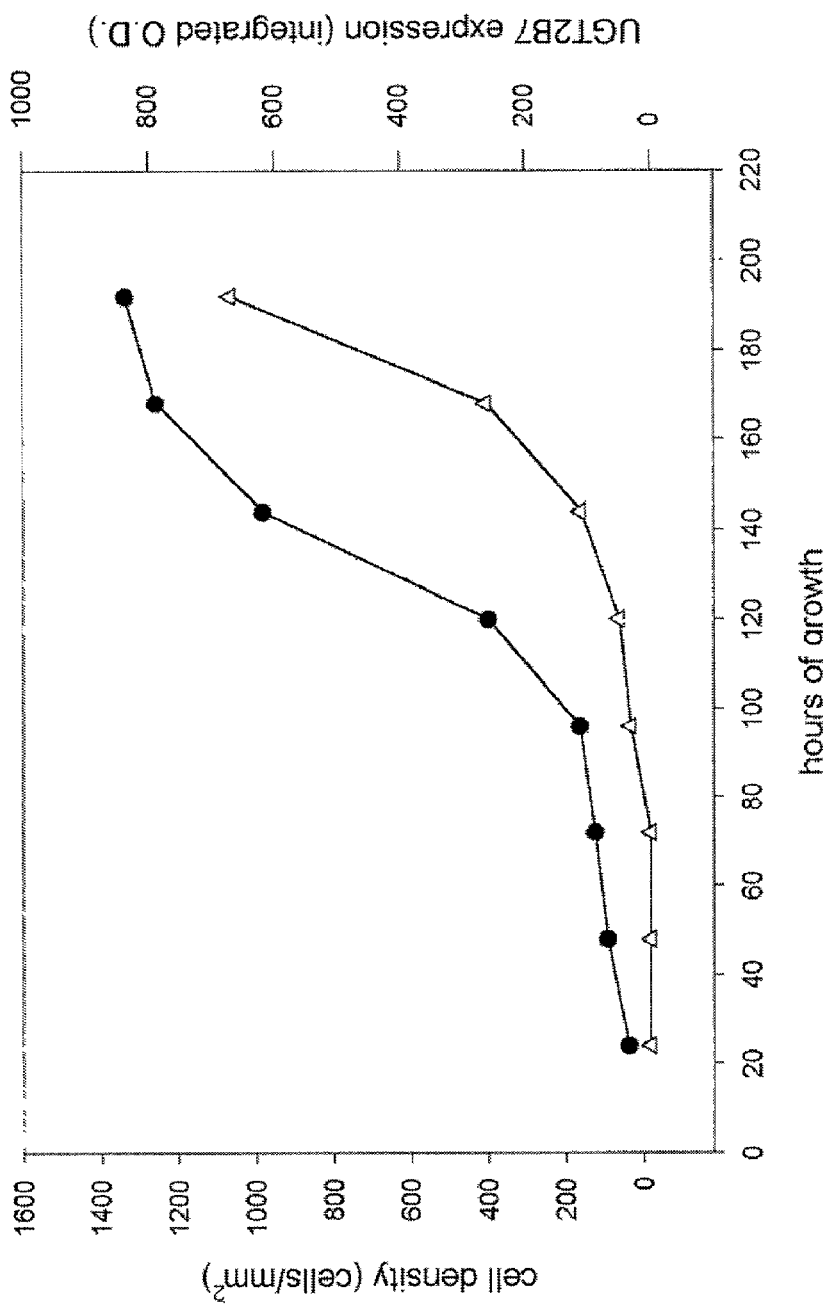
FIG. 2A shows a relationship between cell density (●) and the protein expression (Δ).
Figure 2B:
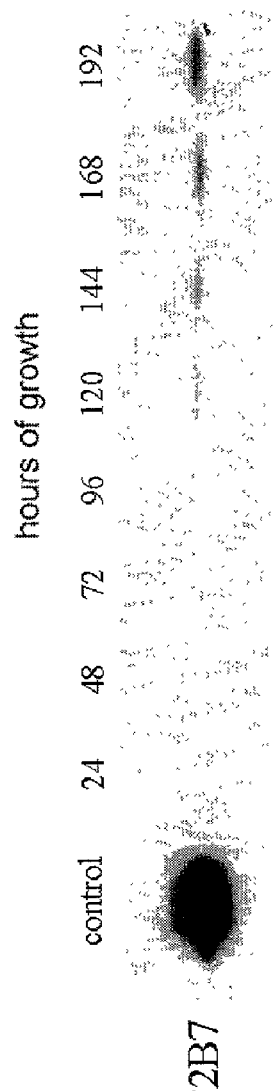
FIG. 2B is a Western blot that shows low expression of endogenous UGT2B7 in JM cells, as compared to the recombinant protein expressed in HK293 cells.

A profile of cell density measured during the experiment (FIG. 2A) showed that logarithmic growth occurs between 96 and 144 hour of culture and then a considerable density-dependent inhibition of growth was observed. Western blot presented on FIG. 2B showed that UDP-glucuronosyltransferase 2B7 protein was not present during the first ~90 hours of growth. Low accumulation of UDP-glucuronosyltransferase 2B7 protein was observed between 96 and 144 hour and ~6-fold increase was observed between 144 and 192 hour. This experiment showed that JM cells express endogenous UDP-glucuronosyltransferase 2B7 protein in a temporal pattern; however, the protein levels were very low as compared with HK293/2B7 control cells expressing the recombinant protein.

A comparison of the growth and protein expression patterns indicates that in the above cell model UDP-glucuronosyltransferase 2B7 protein accumulation correlates with the stationary phase and growth inhibition, but not with exponential cell growth. To check if the absence of UDP-glucuronosyltransferase 2B7 protein in vigorously growing cells results from downregulation of gene expression, Northern blot analysis of UDP-glucuronosyltransferase 2B7 mRNA was carried out in JM cells, as well as in JW and BallardK cell lines. An exon I-specific probe (bases 1–240) and previously established stringent hybrydization conditions were used to avoid cross-hybrydization with homologous UGT mRNA species.

Figure 3:
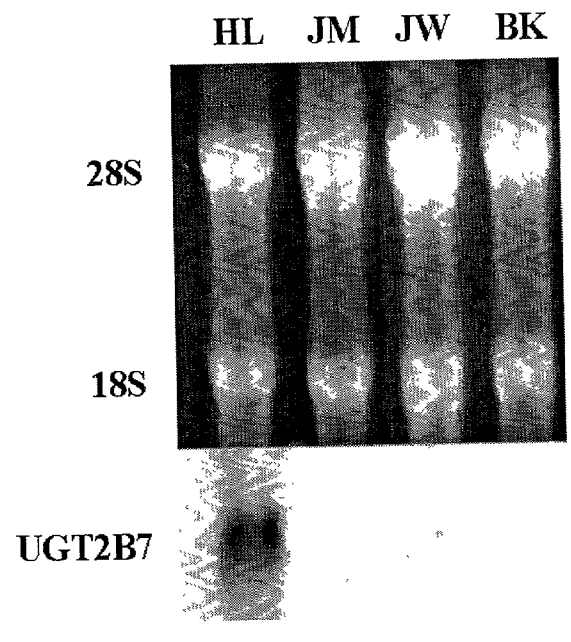
FIG. 3 shows Northern blot analysis of UGT2B7 expression in ovarian cancer cell lines. HL: human liver; JM, JW, BK: ovarian cancer cell lines.

As it is shown on FIG. 3, UDP-glucuronosyltransferase 2B7 message was not detected in all three cell lines. This result indicated that the absence of UDP-glucuronosyltransferase 2B7 protein and lack of enzymatic activity is due to downregulation of gene expression, rather than to the inactivity of the protein, posttranscriptional block in the protein synthesis or protein degradation.

EXAMPLE 3

Overexpressionxpression of UDP-glucuronosyltransferase 2B7 in Ovarian Cancer Cells To test whether downregulation of UDP-glucuronosyltransferase 2B7 may contribute to the cancer phenotype, cellular proliferation and morphology were examined in UDP-glucuronosyltransferase 2B7 stable transformants constructed in JM cells. The UDP-glucuronosyltransferase 2B7 was introduced into JM cells using pCDNA3.1Zeo vector, in which the cDNA is under the control of CMV constitutive promoter and is independent from endogenous regulation. Control cell line was also constructed using empty vector. Following lipofectamine-mediated transfection and zeocin selection, 9 transformants containing UDP-glucuronosyltransferase 2B7 and 13 transformants containing empty vector were isolated. The positive transformants expressed UDP-glucuronosyltransferase 2B7 mRNA at different levels. UDP-glucuronosyltransferase 2B7 message was absent in control cells containing empty vectors.

The present study was focused on one transformant (500-3) which expressed a relatively low amount of UDP-glucuronosyltransferase 2B7 message, and two transformants (500-4 and 500-6) that expressed UDP-glucuronosyltransferase 2B7 transcript at levels comparable to that in human liver.

Figure 4:
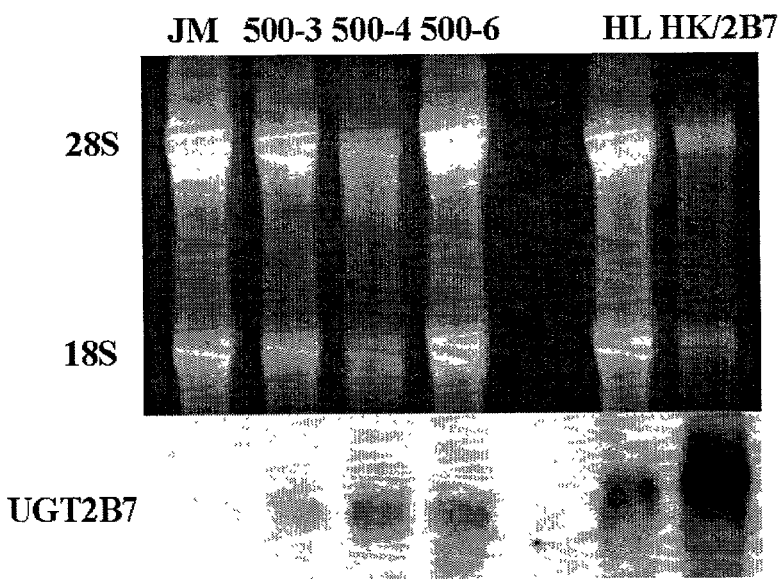
FIG. 4 shows Northern blot analysis of UGT2B7 expression in stable transformants. JM: parental cell line transformed with empty vector; 500-3, 500-4, 500-6: stable transformants; HL: human liver; HK/2B7: HK293 cells expressing the recombinant UGT2B7.

FIG. 4 shows quantitation of UDP-glucuronosyltransferase 2B7 transcript relative to human liver and equalized against ethidium bromide-stained 28S and 18S ribosomal RNA. The 500-3 transformant expressed UDP-glucuronosyltransferase 2B7 message at the 18% level of that in liver, whereas 500-4 and 500-6 transformants expressed UDP-glucuronosyltransferase 2B7 at 55% and 70%, respectively. It is important to stress that levels of expression in the transformants are several fold lower compared to the expression in the standard HK293/UGT2B7 transformants. This makes these transformants a very good model for studying overexpression of UDP-glucuronosyltransferase 2B7 at physiological levels of expression.

Figure 5A:
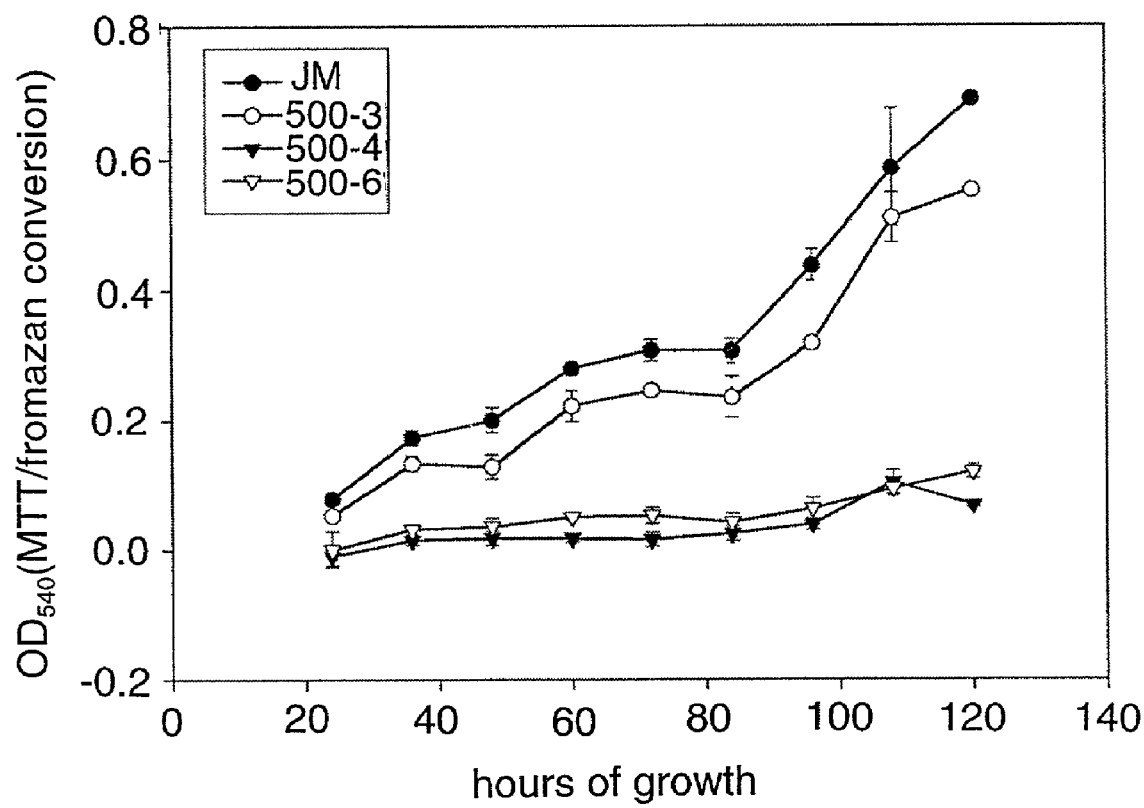
FIG. 5A shows MTT proliferation assay. JM: cancer cells transfected with empty vector; 500-3, 500-4 and 500-6: UGT2B7 stable transformants.

The stable transformants were then analyzed for their capacity to proliferate within 120 hours of culture, a period characterized with negligent expression of the endogenous protein. MTT proliferation assays in three independent experiments revealed a profound effect of UDP-glucuronosyltransferase 2B7 expression on cell proliferation and growth morphology. Results presented in FIG. 5A show that transformants 500-4 and 500-6 were completely blocked in proliferation. Microscopic observations showed a very limited amount of non-adherent cells, indicating that the cells were viable, quiescent or dividing at a low rate, rather than proliferating and dying due to accelerated apoptosis or necrosis. However, the number of non-adherent cells was markedly increased between 100 and 120 hour of culture. Transformant 500- 3 exhibited a proliferation profile very similar to that of the JM-1 control cell line, although the average proliferation rate was ~25% lower. A comparison of the UDP-glucuronosyltransferase 2B7 message level and proliferation patterns suggests a dose-dependent effect of UDP-glucuronosyltransferase 2B7 expression on cell divisions.

Figure 5B:
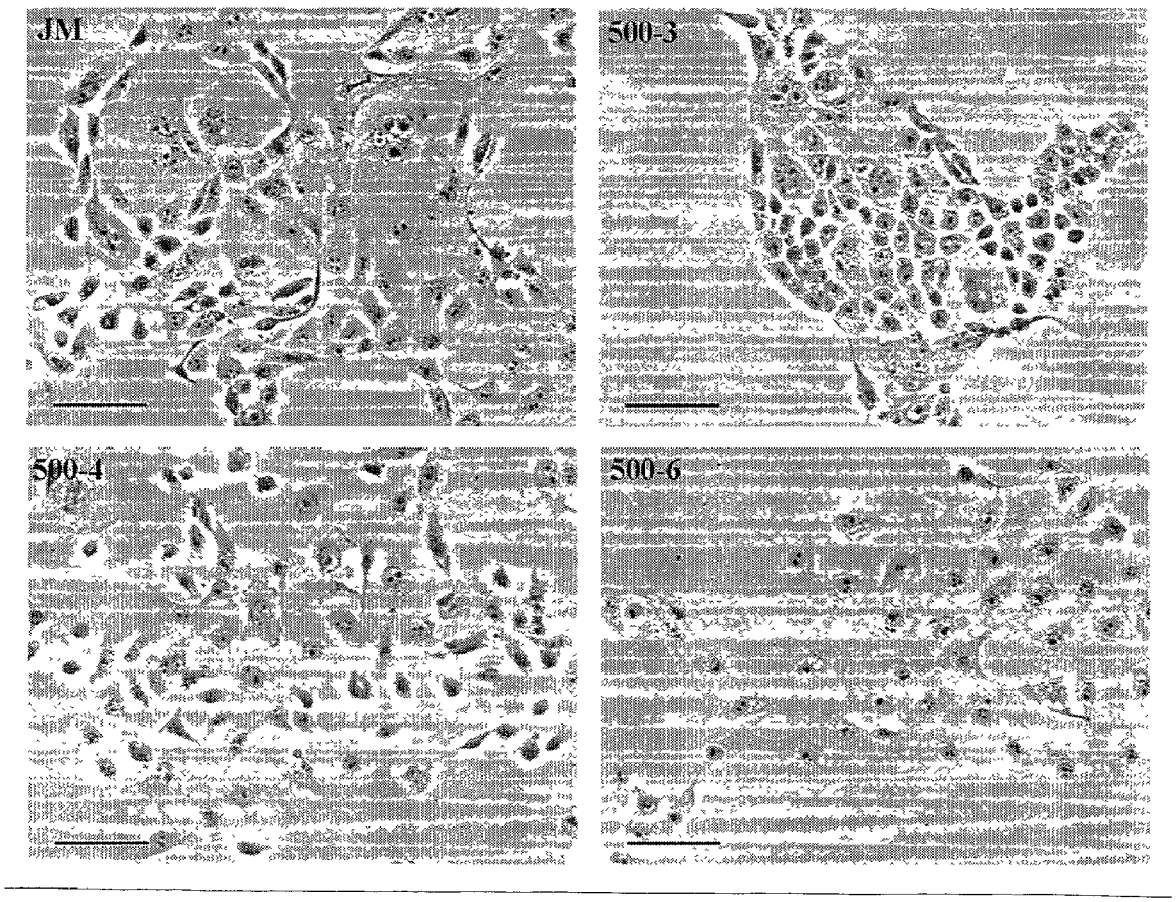
FIG. 5B shows growth morphology of stable transformants and JM control cells.

Growth inhibition was also associated with changes in cell morphology as presented in FIG. 5B. The JM control cell line consists of two cell populations that exist in culture in a constant proportion: a moderate population of multinuclear cells 100–200 μm in diameter, and numerous elongated mono- or dinuclear cells up to 50 μm in length. 500-3 cell line revealed an aggregation pattern 110 very similar to that of the JM cell line; however both cell types were reduced in size by ~50%. Remarkable changes were observed for 500-4 and 500-6 transformants. The number of multinuclear cells was drastically reduced and the cells lost the ability to form colonies or aggregates, thus demonstrating a dispersed growth pattern. These observations suggest that the extent of changes in growth morphology may be associated with the expression level of UDP-glucuronosyltransferase 2B7, and support the results on the proliferation of the transformants.

EXAMPLE 4

Reduction of Lipid Content in UDP-Glucuronosyltransferase 2B7 Stable Transformants The cytoplasm of JM cells contain a large amount of lipid-containing microvesicles as it was determined by a positive Oil Red O staining. The amount of these microvesicles was greatly reduced in the transformants studied above. To further examine this effect, total lipid content in cell lysates were determined using a semi-enzymatic triglyceride assay. This method relies on hydrolysis of glycerides at low pH and enzymatic determination of glycerol concentration. Microscopic evaluation of the cells stained with Oil Red O was also carried out.

Figure 6A:
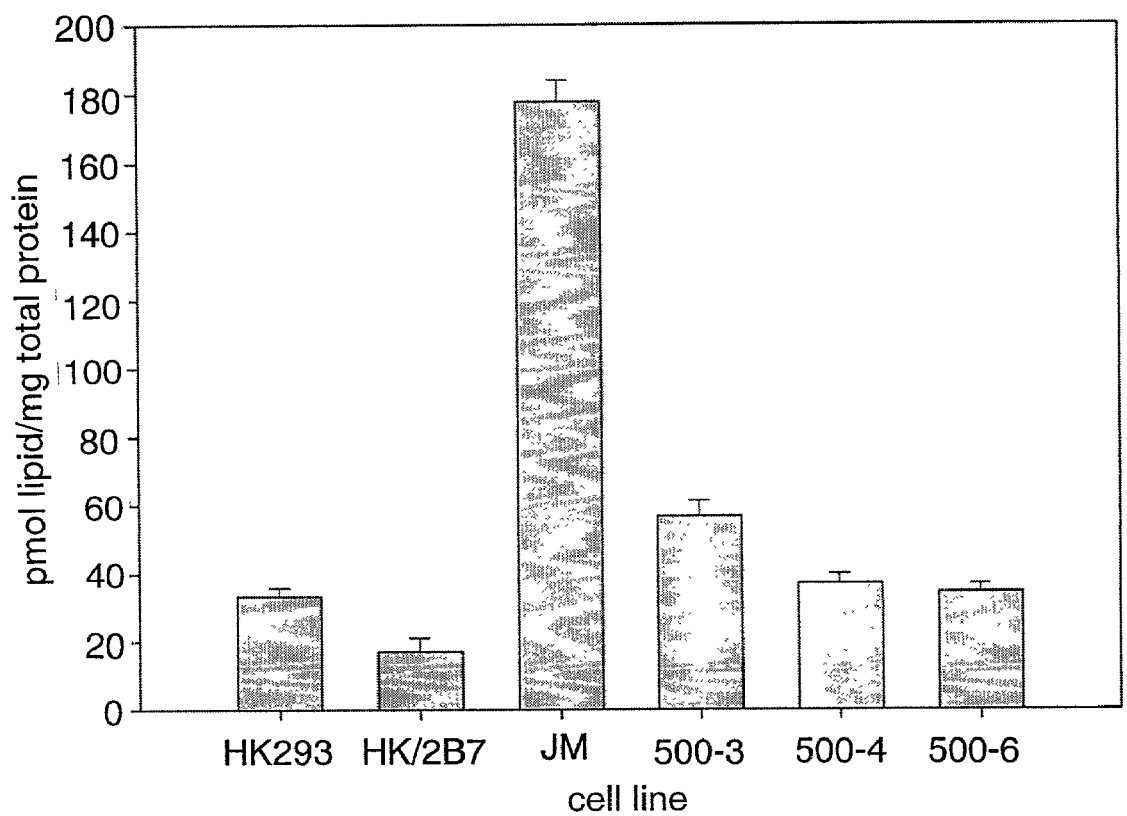
FIG. 6A shows lipid content determined for HK293: non transfected control cells; HK/2B7: HK293 transfected with UGT2B7; JM: ovarian cancer cell line; 500-3, 500-4 and 500-6: UGT2B7 stable transformants of JM cells.
Figure 6B:
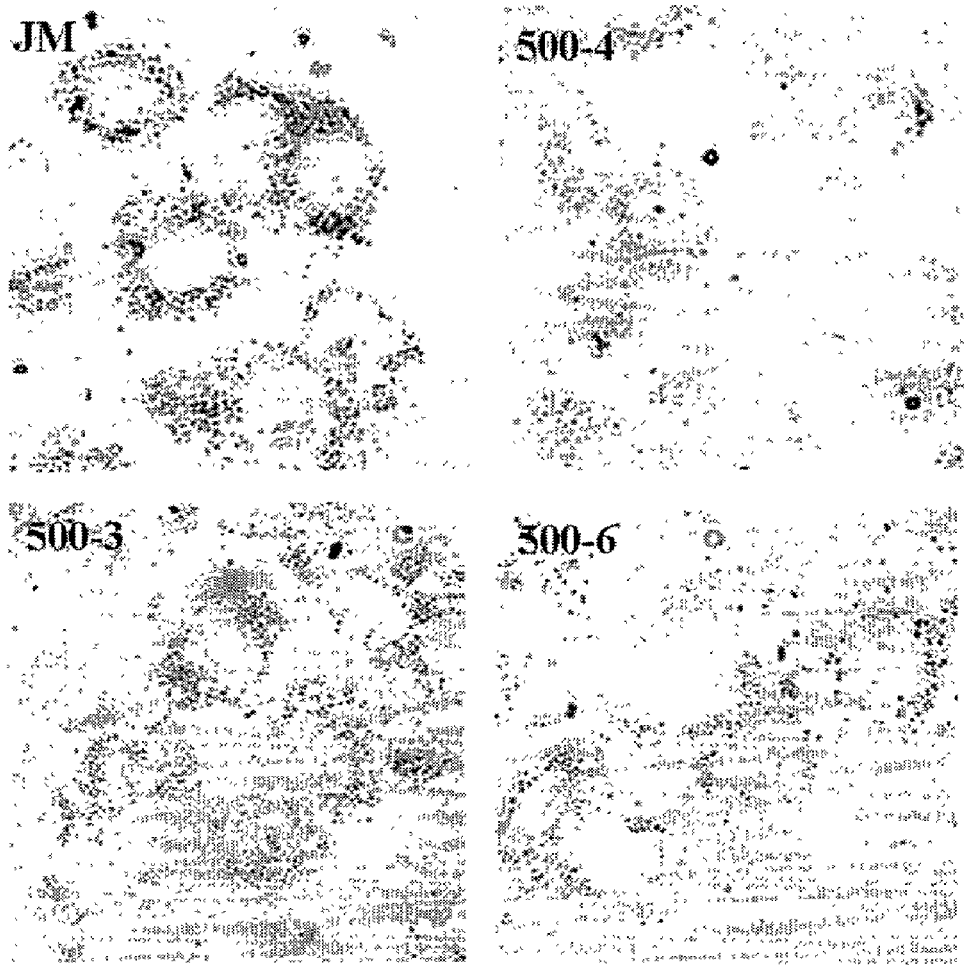
FIG. 6B shows lipid-containing microvesicles stained with Oil Red O in UGT2B7 stable transformants and non transfected JM cells.

Average microscopic images presented in FIG. 6B show that JM cells contained intensely stained microvesicles organized in a characteristic punctuated pattern in the perinuclear zone. 500-3 cells displayed a modest reduction of staining, whereas 500-4 and 500-6 cells showed a significant decrease in lipid staining as compared to control cells.

Results obtained with the lipid content assay corroborated with microscopic observations (FIG. 6A). High lipid content averaging 177.6 pm/mg of protein in JM-1 cells was reduced 3-fold in 500-3 cells and showing a 5-fold reduction in 500-4 and 500-6 cells. Interestingly, the reduced lipid concentration in 500-4 and 500-6 cells was very similar to the "normal" content measured in non-transfected HK293 cells. HK293 cells and HK293/UGT2B7 stable transformants were used as control in this assay and there was a 50% reduction of lipids in HK293/UGT2B7 transformed cells;

however this was not associated with cell proliferation or growth morphology. Similarly, as it was in the case of proliferation experiments, the reduction of total lipid content correlates with increased expression of UDP-glucuronosyltransferase 2B7, and apparently results from an altered fatty acid metabolism via glucuronidation.

EXAMPLE 5

The Effect of Inactivation of UDP-Glucuronosyltransferase 2B7

The effects of reintroducing UDP-glucuronosyltransferase 2B7 protein into otherwise non-expressing JM-1 ovarian cancer cells described above indicated that the absence of this isoform may contribute to the cancer phenotype. Thus, oligonucleotide-mediated inactivation of UDP-glucuronosyltransferase 2B7 mRNA was carried out to verify this hypothesis. Conditions for lipofectamine-mediated transfection using pEGFP plasmid (green fluorescent protein) were optimized and it was established that transfection is most efficient at ~60% cell confluence, yielding up to 50% transformants. These conditions were used in the inactivation experiment. 500-4 cells were plated at high density in 96-well plates to achieve ~60% confluence after 24 hours of incubation. 500-4 cells were then transfected with 10 nM antisense oligonucleotide which is complementary to the +774/+803 region of UDP-glucuronosyltransferase 2B7 mRNA and incubated for the following 96 hours without the medium change. Controls in this experiment were 500-4 cells transfected in the same conditions with a sense oligonucleotide homologous to +38/+56 and JM-1 cells transfected with the antisense oligonucleotide. Cell proliferation was measured using MTT assay at 24 hour intervals. 500-4 cells treated with antisense oligonucleotide were expected to have increased proliferation due to inactivation of the inhibitory effects of UDP-glucuronosyltransferase 2B7 on cell growth, whereas no effect was expected in 500-4 cells treated with the sense oligonucleotide or JM cells treated with the antisense oligonucleotide.

Figure 7:
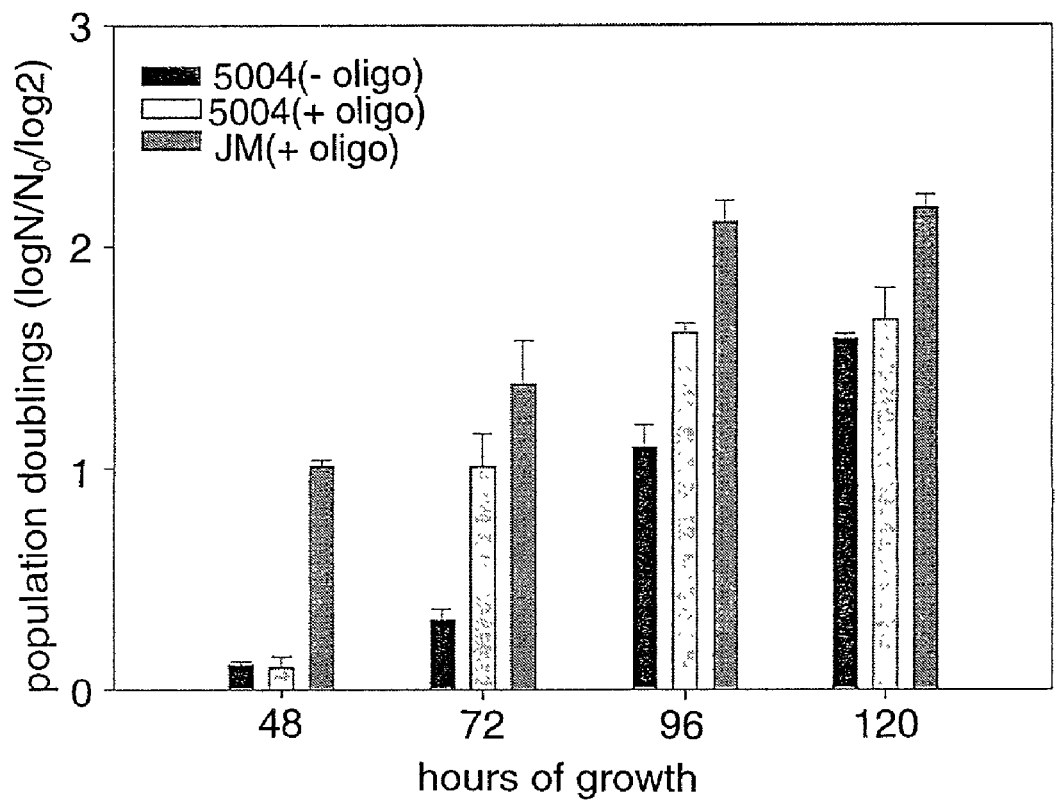
FIG. 7 shows proliferation of ovarian cancer cells treated with oligonucleotide that inactivates UGT2B7 mRNA. Bars represent mean population doublings calculated for three experiments. Dark gray: JM cells treated with oligo; black: 500-4 cells not treated; light gray: 500-4 cells treated with oligo.

Results from three independent experiments shown in FIG. 7 demonstrate that transfection of 500-4 cells with antisense oligonucleotide significantly increase mean population doublings (MPD) during 48 hours following transfection as compared to control cells. At 48 hour time point (24 hours after transfection), 500-4 cells transfected with sense and antisense oligonucleotide proliferated at similar low rate as compared to JM-1 control. At 72 hour 500-4 cells transfected with antisense oligonucleotide exhibited a significant acceleration in growth (MPD=1.0) that approximated the growth rate of JM cells (MPD=1.37). Proliferation of 500-4 cells transfected with sense oligonucleotide remained on the low level (MPD=0.35). At 96 hour of the experiment a noticeable increase in proliferation of 500-4 control cells was observed, while 500-4 cells transfected with antisense oligonucleotide slowed down in growth. At the 120 hour time point (96 hour after transfection) both 500-4 cells reached the same dynamics of proliferation. This experiment showed that inactivation of UDP-glucuronosyltransferase 2B7 mRNA transiently reversed slow growth phenotype of 500-4 cells to fast growth parental phenotype of JM-1 cells.

EXAMPLE 6

HER2/Neu Mediates Downregulation of UDP-glucuronosyltransferase in Ovarian Cancer Cells UDP-glucuronosyltransferase 2B7 protein is not expressed in vigorously growing cells, however a moderate expression of this protein is observed in confluent cultures characterized by slow cell proliferation. It is possible that upregulation of UDP-glucuronosyltransferase 2B7 in this growth phase may be mediated by transduction signaling. Ovarian cancer cells express HER2/Neu protein, a tyrosine kinase receptor which is involved in cell proliferation (Kurebayashi, 2001) and tumor aggressiveness.

To test the role of HER2/Neu in regulating UDP-glucuronosyltransferase 2B7 expression, HER2/Neu protein was inactivated with a specific monoclonal antibody herceptin, and the expression of UDP-glucuronosyltransferase 2B7 and UDP-glucuronosyltransferase 1A6 was analyzed. JM cells were grown to ~75% confluence and treated with herceptin at 1:500 dilution for 48 hr. Untreated cells and cells treated with anti-CD20 lymphocyte antigen antibody were used as controls.

Figure 8:
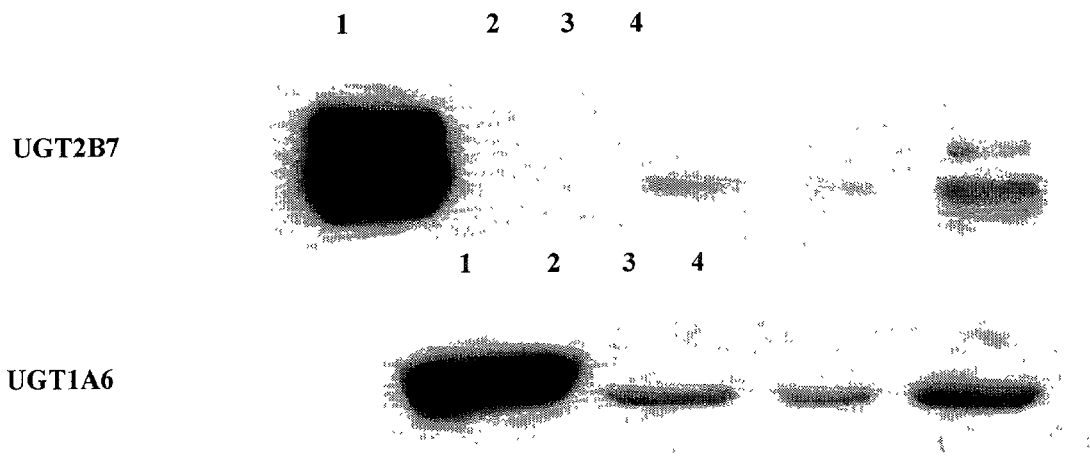
FIG. 8 shows Western blot analysis of UGT2B7 and UGT1A6 in JM cell line treated with anti-Her2 antibody. Lane 1: control recombinanat protein; lane 2: untreated cell culture; lane 3: cell culture treated with anti-CD20 antibody; lane 4: cell culture treated with herceptin (anti-HER2).

Western blot and densitometry analysis revealed a ~5 fold increase in UDP-glucuronosyltransferase 2B7 protein expression and a ~2 fold increase in UDP-glucuronosyltransferase 1A6 protein after HER2/Neu inactivation (FIG. 8). This result strongly suggests that HER2-mediated signal transduction is involved in regulation of UDP-glucuronosyltransferases.

EXAMPLE 7

Figure 10:
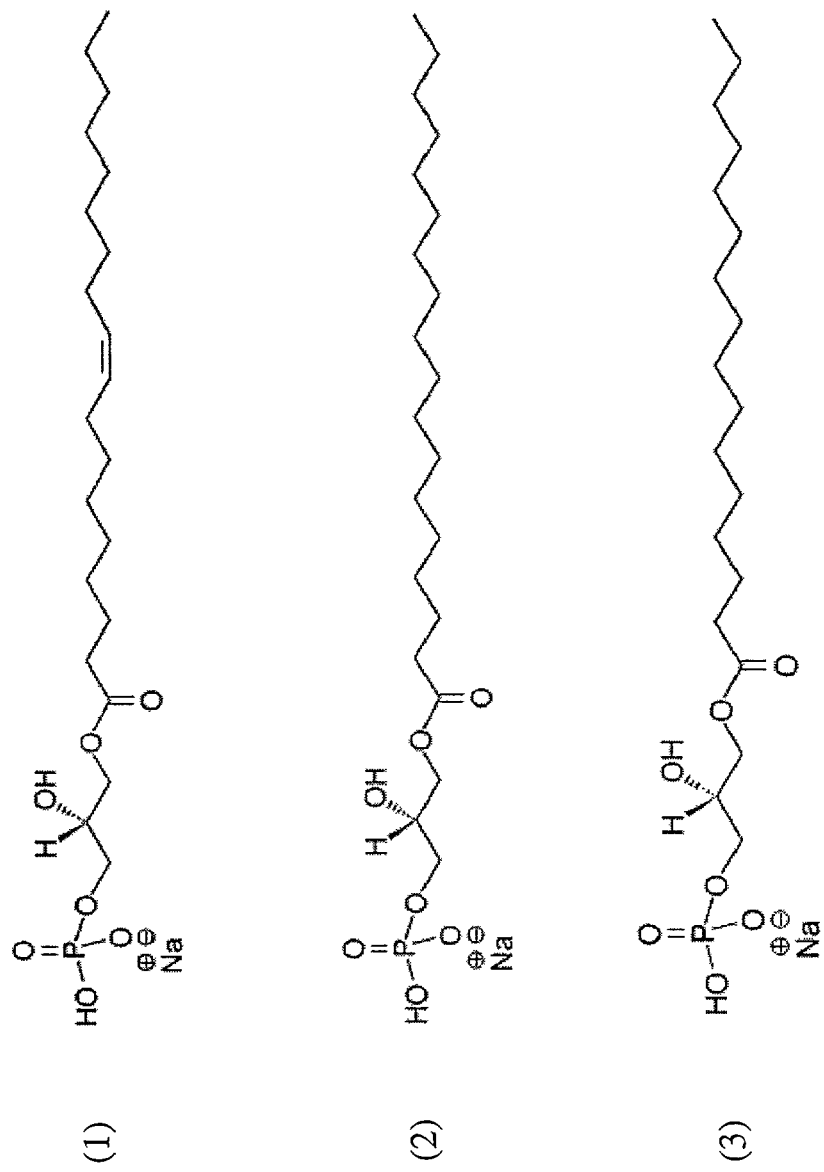
FIG. 10 shows structures of lysophosphatidic acid molecules used in glucuronidation assay. 1: oleoyl-LPA; 2: stearoyl-LPA; 3: palmitoyl-LPA.

Glucuronidation of Lysophosphatidic Acid by Recombinant UDP-Glucuronosyltransferase 2B7 Protein Lysophosphatidic acid (LPA) stimulates lysophosphatidic acid receptors which in turn activate PKC and Ras-MAPK signalling pathways. Lysophosphatidic acid is a lipid second messenger involved in progression of malignant ovarian cancer. Cellular effects of lysophosphatidic acid accumulation include stimulation of cell proliferation, inhibition of apoptosis and increased invasiveness of cancer cells. It was hypothesized that anti-proliferative activity of UDP-glucuronosyltransferase 2B7 in the ovarian cancer cell model described above may be associated with inactivation of lysophosphatidic acid through glucuronidation. Thus, in vitro glucuronidation experiments on three different lysophosphatidic acid compounds (FIG. 10) was conducted using human liver microsomes and a recombinant UDP-glucuronosyltransferase 2B7 expressed in HK293 cells.

Figure 9A:
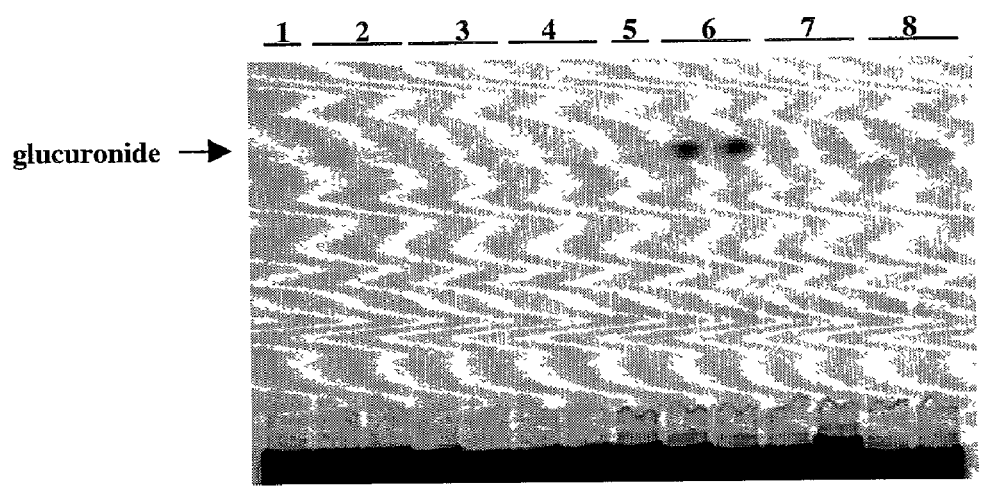
FIG. 9A shows glucuronidation of lysophosphatidic acid (LPA) by a recombinant UGT2B7 and human liver microsomes. Lanes 1–4: recombinant UGT2B7; lanes 5–8: human livers microsomes. Lanes 1 and 5 are reactions w/o substrate; 2 and 6: oleoyl-LPA; 3 and 7: stearoyl-LPA; 4 and 8: palmitoyl-LPA. Reactions with substrates were run in duplicates.
Figure 9B:
FIG. 9B shows de-glucuronidation of oleoyl-LPA-glucuronide by bacterial beta-glucuronidase. Lane 1: glucuronidation reaction w/o substrate; lane 2: oleoyl-LPA-glucuronide; lane 3: oleoyl-LPA-glucuronide w/o beta-glucuronidase; lane 4: oleoyl-LPA-glucuronide treated with beta-glucuronidase.

Results presented in FIG. 9A clearly show that UDP-glucuronosyltransferase 2B7 actively glucuronidated oleoyl-lysophosphatidic acid but not stearoyl-lysophosphatidic acid and palmitoyl-lysophosphatidic acid. The same activity profile was obtained using human liver microsomes that contain several UDP-glucuronosyltransferase activities including that of UGT2B7. Specific activities measured for both assays were 250 pmol/min/mg and 560 pmol/min/mg for the recombinant enzyme and liver microsomes, respectively. Interestingly, only oleoyl-lysophosphatidic acid, which contains unsaturated fatty acid chain, undergoes glucuronidation in this system, whereas palmitoyl- and stearoyl-lysophosphatidic acid, which both contain saturated fatty acid chain, do not. The result presented in FIG. 9B shows that oleoyl-lysophosphatidic acid glucuronide can be hydrolyzed by a beta-glucuronidase, thus confirming the specificity and enzymatic origin of this compound.

The following references were cited herein:

Bock. (1991). *Critical Reviews in Biochemistry & Molecular Biology,* 26:129–50.
Bock et al. (1999). *Drug Metabolism Reviews,* 31:411–22.
Gestl et al. (2002). *American Journal of Pathology,* 160: 1467–79.
Grant & Bell. (2000). *Molecular Carcinogenesis,* 29:198–204.
Guillemette et al. (2000). *Cancer Research,* 60:950–6.
Kuhajda. (2000). *Nutrition,* 16:202–8.
Kurebayashi. (2001). *Breast Cancer,* 8:45–51.
Radominska-Pandya et al. (1999a). *Drug Metabolism Reviews,* 31:817–99.
Jude et al. (2001). *Archives of Biochemistry & Biophysics,* 389:176–86
Strassburg et al. (1997). *Cancer Research,* 57:2979–85.
Xu et al. (2001). *Journal of the Society for Gynecologic Investigation,* 8:1–13.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for detecting malignant ovarian hyperplasia, comprising the steps of:
    (a) isolating protein from ovarian tissue sample; and
    (b) detecting UDP-glucuronosyltransferase 2B7 protein in said sample, wherein a decrease of UDP-glucuronosyltransferase 2B7 protein expression in said sample as compared to UDP-glucuronosyltransferase 2B7 protein expressed in normal ovarian tissue is indicative of the presence of malignant ovarian hyperplasia.

2. The method of claim 1, wherein said detection of UDP-glucuronosyltransferase 2B7 protein is by Western blot analysis.

* * * * *